US00PP17942P2

(12) United States Plant Patent
Evers

(10) Patent No.: US PP17,942 P2
(45) Date of Patent: Aug. 21, 2007

(54) GROUND COVER ROSE PLANT NAMED 'TAN98110'

(50) Latin Name: *Rosa hybrida*
Varietal Denomination: TAN98110

(75) Inventor: Hans Jurgen Evers, Uetersen (DE)

(73) Assignee: Rosen Tantau Mathias Tantau Nachfolger, Uetersen (DE)

( * ) Notice: Subject to any disclaimer, the term of this patent is extended or adjusted under 35 U.S.C. 154(b) by 300 days.

(21) Appl. No.: 10/968,562

(22) Filed: Oct. 18, 2004

(51) Int. Cl.
*A01H 5/00* (2006.01)

(52) U.S. Cl. ..... Plt./126

(58) Field of Classification Search ..... Plt./124, Plt./126, 133, 135, 144, 146
See application file for complete search history.

*Primary Examiner*—Howard J. Locker
(74) *Attorney, Agent, or Firm*—Klarquist Sparkman LLP

(57) ABSTRACT

A new and distinct ground cover rose plant having very robust growth and high resistance to blackspot and powdery mildew.

3 Drawing Sheets

Genus and species: *Rosa hybrida.*
Varietal denomination: 'TAN98110'.

SUMMARY OF THE INVENTION

The present invention relates to a new and distinct variety of ground cover rose plant named 'TAN98110', which was originated by me by crossing 'TANmurse' (Schneesturm) (unpatented) with an unnamed, unpatented variety.

BACKGROUND OF THE INVENTION

The primary objective of this breeding was to produce a new ground cover rose variety which is very robust and resistant to black spot and powdery mildew.

BRIEF SUMMARY OF THE INVENTION

The objective was substantially achieved, along with other desirable improvements, as evidenced by the unique combination of characteristics described hereinafter that are outstanding in the new variety and that distinguish it from its parents, as well as from all other varieties of which I am aware.

Asexual reproduction of this new variety by grafting onto *R.canina* rootstock at Uetersen, Germany, shows that the foregoing and all other characteristics and distinctions come true to form and are established and transmitted through succeeding propagations.

Comparison with Parents

'TAN98110' has brighter color of flower as compared to its pollen parent and taller growth as compared to its seed parent.

Comparison with Similar Variety

'TAN98110' is similar to the variety 'TANmurse' but its flower color is brighter than that of 'TANmurse'.

BRIEF DESCRIPTION OF THE ILLUSTRATIONS

The accompanying illustrations show typical specimens of the flowers of this new variety depicted in color as nearly true as it is reasonably possible to make the same in color illustrations of this character.

DETAILED BOTANICAL DESCRIPTION

Figure 1:
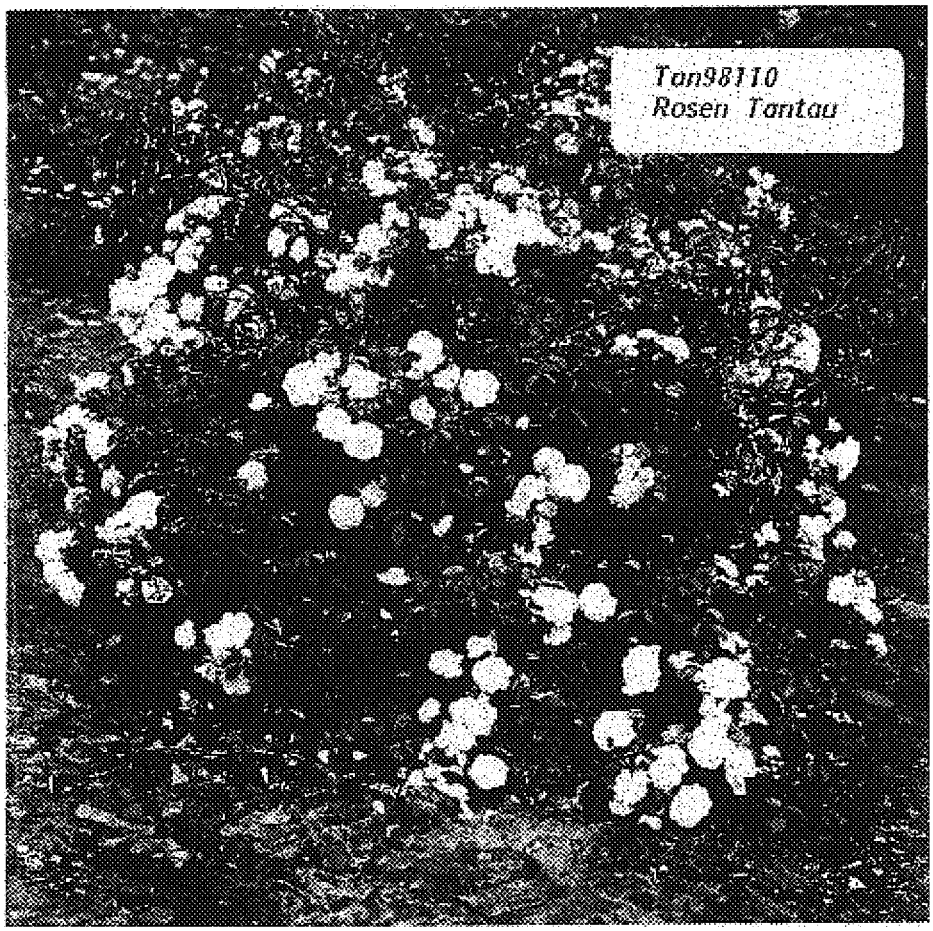
FIG. 1 is a view of a mature plant.
Figure 2:
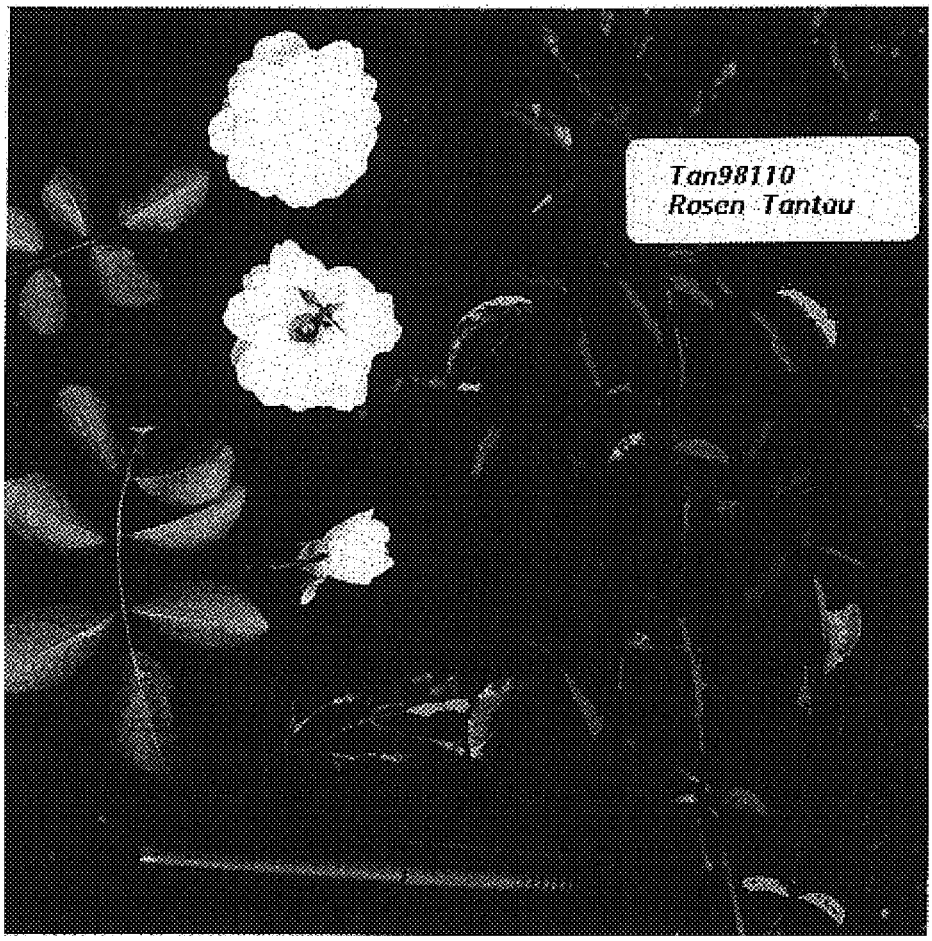
FIG. 2 is a view showing parts of a mature plant with a pen in the foreground to indicate the relative sizes of the plant parts shown.
Figure 3:
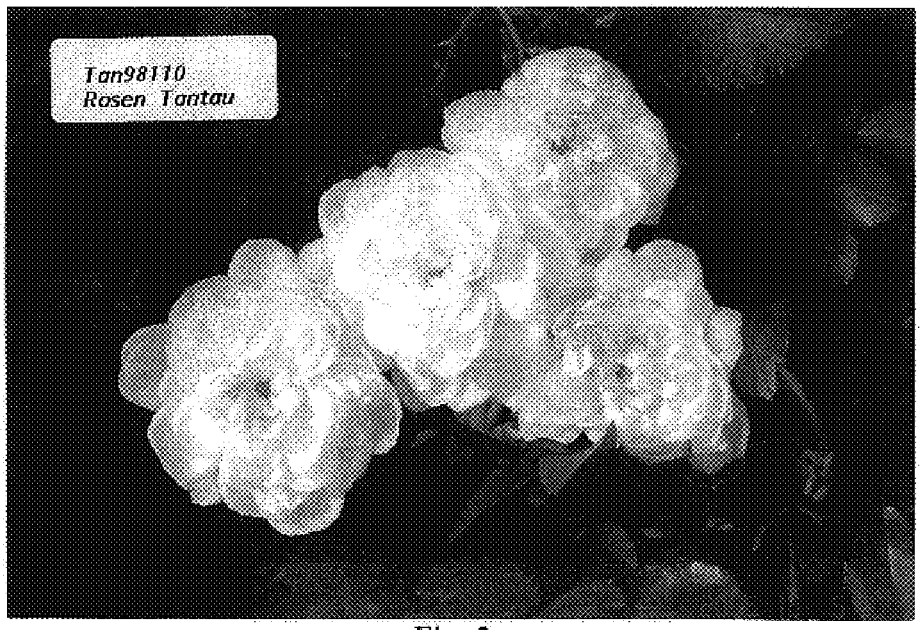
FIG. 3 is a view from above of a cluster of blooms.
Figure 4:
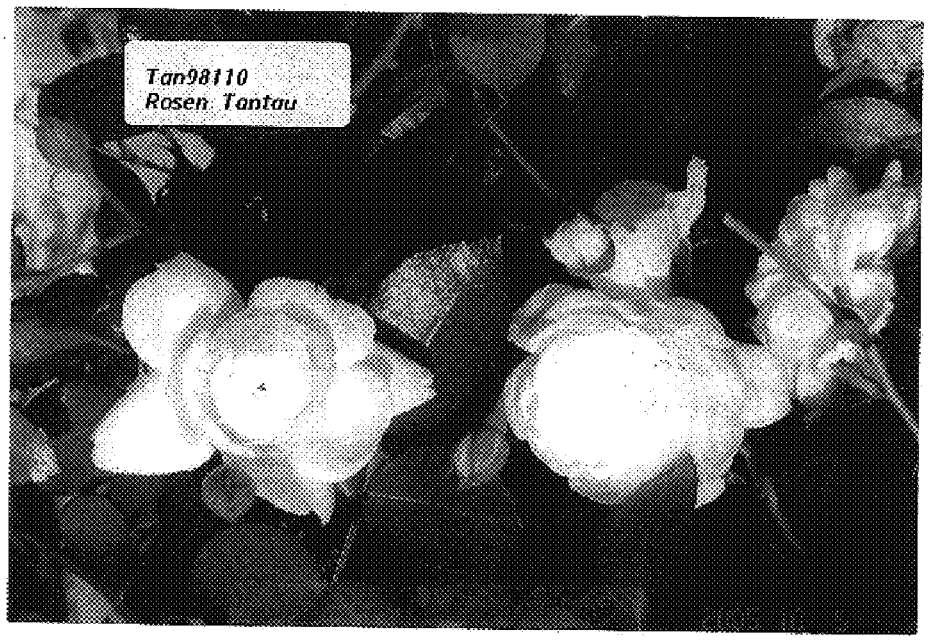
FIG. 4 is a view from above showing portions of the foliage and blooms in various stages of development.

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—'TANmurse'.
*Pollen parent.*—Unnamed variety.

FLOWER

Observations were made from plants two years of age grown in a garden environment at Uetersen, Germany, on a day when the cloud cover was about 28 percent and ambient temperature was about 24 degrees C.

Blooming habit: Summer and Fall.

Bud:
*Size.*—About 1.2 cm long and 0.4 cm in diameter when the petals start to unfurl.
*Form.*—The bud form is pointed ovoid.
*Color.*—When sepals first divide, bud color is Orange Group 29D. When half blown, the upper sides of the petals are Orange Group 29D; and the lower sides of the petals are Orange Group 27B.

*Sepals.*—Color: Upper surface: Green Group 144C. Lower surface: Green Group 144A. Length: 1.9 cm. Width: 0.4 cm. Shape: Elongate, pointed. Surface texture: Smooth. There are three lightly appendaged sepals. There are two unappendaged sepals with glandular edges.

*Receptacle.*—Color: Green Group 144A. Shape: Funnel. Size: Small, about 0.4 cm×0.2 cm.

*Peduncle.*—Length: Short, averaging about 6 cm. Surface: Smooth. Color: Yellow Green Group 146A. Strength: Slender.

*Pedicel.*—Length: 4.7 cm. Color: Green Group 138A.

Bloom:

*Size.*—Small. Average open diameter is about 4.3 cm.

*Borne.*—In clusters of 10–15 buds.

*Stems.*—Strength: Weak. Average length is about 16 cm and diameter 0.2 cm.

*Form.*—When first open: Rosette shaped bloom with petals flat in aspect; bloom flattens with age.

*Petalage.*—Number of petals under normal conditions: 26.

*Color.*—The upper sides of the petals are Orange Group 27C. The reverse sides of the petals are Orange Group 27B. The major color on the upper side is Orange Group 27C. The color of the buds and open flowers is strongly dependent upon the ambient temperature and light level. The warmer and brighter it is, the brighter the flower color.

*Variegations.*—None.

*Fade.*—Petals fade to White Group 155A, particularly under warm, bright conditions.

*Fragrance.*—None.

Petals:

*Texture.*—Thin.

*Surface.*—Smooth.

*Shape.*—Oval.

*Margin.*—Smooth.

*Apex shape.*—Pointed.

*Base shape.*—Blunt.

*Form.*—Flat.

*Arrangement.*—Informal.

*Petaloids.*—Number: 14. Color: Orange Group 27C.

*Persistence.*—Petals drop off cleanly before drying.

*Lastingness.*—On the plant: Fair (about 8 days). As a cut flower: Short, (about 3 days).

Reproductive parts:

*Stamens.*—Number: 12. Length: 0.4 cm.

*Anthers.*—Length: 0.1 cm. Color: Yellow Group 3A. Arrangement: Tucked in calyx or partly so.

*Filaments.*—Color: Yellow Group 3A. Length: 0.3 cm.

*Pollen.*—Color: Yellow-Orange Group 14A.

Pistils:

*Number.*—8.

*Length.*—0.4 cm.

*Styles.*—Color: Yellow Group 13A. Length: 0.3 cm.

*Stigmas.*—Color: Yellow-Orange Group 14A. Length: 0.4 cm.

*Hips.*—None produced.

PLANT

Form: Bush.

Growth: Medium.

Mature plant: Height: 70 cm. at 4 years.

*Width.*—50 cm.

Rootstock: *R.canina.*

Foliage: Number of leaflets on normal mid-stem leaves: 7.

*Size.*—Small (7 cm long×3.4 cm wide).

*Quantity.*—Normal.

*Color.*—New foliage: Upper side: Green Group 144B. Lower side: Green Group 141C. Old foliage: Upper side: Green Group 141A. Lower side: Green Group 141C. Foliage exhibits a sheen.

Leaflets: Upper leaflet surfaces exhibit a glossiness or sheen.

*Size.*—About 3 cm long×2 cm wide.

*Shape.*—Elliptic.

*Base shape.*—Rounded.

*Apex shape.*—Cuspidate.

*Texture.*—Upper side: Leathery.

*Edge.*—Serrated.

*Serrations.*—Single.

*Petiole.*—Color: Green Group 138A.

*Petiole rachis.*—Color: Green Group 138A. Underside: Smooth.

*Stipules.*—Smooth. Length: 2 cm.

*Disease resistance.*—Resistant to mildew, blackspot and rust under normal growing conditions.

*Vein color.*—Green Group 138A.

Wood:

*New wood.*—Color: Green Group 138A. Bark: Smooth.

*Old wood.*—Color: Greyed-Orange Group 176B. Bark: Rough.

Prickles:

*Quantity.*—On main canes from base: Five per internode.

*Form.*—Hooked downward.

*Length.*—0.4 cm.

*Color when young.*—Greyed-Red Group 178A.

*Color when mature.*—Greyed-Purple Group 184A.

Small prickles:

*Quantity.*—On main stalks: Few. On laterals: None.

*Color when young.*—Greyed-Purple Group 183D.

*Color when mature.*—Greyed-Orange Group 176A.

Winter hardiness: Not tested.

I claim:

1. A new and distinct variety of ground cover rose plant, substantially as herein shown and described, and characterized particularly by its very robust growth and high resistance to blackspot and powdery mildew.

* * * * *